US009772313B2

(12) United States Patent
Blom

(10) Patent No.: US 9,772,313 B2
(45) Date of Patent: Sep. 26, 2017

(54) METHOD AND APPARATUS FOR IDENTIFYING SHIM GEOMETRIES

(71) Applicant: The Boeing Company, Chicago, IL (US)

(72) Inventor: Adriana Willempje Blom, Shoreline, WA (US)

(73) Assignee: THE BOEING COMPANY, Chicago, IL (US)

( * ) Notice: Subject to any disclaimer, the term of this patent is extended or adjusted under 35 U.S.C. 154(b) by 223 days.

(21) Appl. No.: 14/691,984

(22) Filed: Apr. 21, 2015

(65) Prior Publication Data
US 2016/0313287 A1 Oct. 27, 2016

(51) Int. Cl.
G01B 17/02 (2006.01)
G01N 29/04 (2006.01)
G01B 17/00 (2006.01)
B64C 1/12 (2006.01)
G01B 7/14 (2006.01)

(52) U.S. Cl.
CPC .......... *G01N 29/043* (2013.01); *G01B 17/00* (2013.01); *B64C 1/12* (2013.01); *G01B 7/14* (2013.01); *G01N 2291/044* (2013.01); *G01N 2291/106* (2013.01); *G01N 2291/2694* (2013.01)

(58) Field of Classification Search
CPC ...................................... G01B 17/00
USPC ................................... 73/597, 598
See application file for complete search history.

(56) References Cited

U.S. PATENT DOCUMENTS

| 4,184,373 | A | 1/1980 | Evans et al. |
| 5,099,849 | A * | 3/1992 | Rossman ............. A61B 8/0875 600/442 |
| 5,385,050 | A * | 1/1995 | Roberts .................. G01B 17/00 33/783 |
| 7,974,722 | B2 | 7/2011 | Boyl-Davis et al. |
| 8,756,792 | B2 | 6/2014 | Boyl-Davis et al. |
| 2008/0205763 | A1 | 8/2008 | Marsh et al. |

(Continued)

FOREIGN PATENT DOCUMENTS

| DE | 102009060106 A1 | 6/2011 |
| EP | 2727711 A1 | 5/2014 |
| WO | WO 0218872 A1 | 3/2002 |

OTHER PUBLICATIONS

Extended European Search Report, dated Aug. 24, 2016, regarding Application No. 16154624.7, 13 pages.

(Continued)

*Primary Examiner* — John Chapman, Jr.
(74) *Attorney, Agent, or Firm* — Yee & Associates, P.C.

(57) ABSTRACT

A method and apparatus for identifying shim geometries. A first part and a second part are assembled with a couplant positioned between the first part and the second part at a shim location, at which a shim is to be installed, to form an assembly. A pulse of ultrasonic energy is sent into the assembly at each of a set of selected locations along the assembly corresponding to the shim location using an ultrasonic device. A plurality of echoes is detected for each of the set of selected locations using data generated by the ultrasonic device in response to the ultrasonic device receiving reflections of the ultrasonic energy. A geometry for the shim is identified based on the plurality of echoes detected at each selected location of the set of selected locations.

18 Claims, 10 Drawing Sheets

(56) References Cited

U.S. PATENT DOCUMENTS

2014/0303764 A1 10/2014 Boyl-Davis et al.
2014/0365061 A1 12/2014 Vasquez et al.

OTHER PUBLICATIONS

Dalin et al. "Measurement of the thickness of U-30MES-5NT and VGM-L sealing compound layers in aircraft products using the ultrasonic nondestructive testing method", Polymer Science Series D; Glues and Sealing Materials, Oct. 2012, vol. 5, Iss. 4, pp. 305-308. Abstract Only.
Lagally et al., "Predictive Shimming for Flexible Surfaces," U.S. Appl. No. 14/252,997, filed Apr. 15, 2014, 59 pages.
De Groot, "Unusual techniques for absolute distance measurement," Society of Photo-Optical Instrumentation Engineers, vol. 40, Issue 1, Jan. 2001, pp. 28-32.
Nozaki et al., "787 wing skin automatic 3D measurement system with Laser Radar," Hitachi Engineering & Services Co., Ltd., Jul. 2008, 44 pages.

\* cited by examiner

US 9,772,313 B2

METHOD AND APPARATUS FOR IDENTIFYING SHIM GEOMETRIES

BACKGROUND INFORMATION

1. Field

The present disclosure relates generally to shims and, in particular, to identifying shim geometries. Still more particularly, the present disclosure relates to a method and apparatus for measuring a shim geometry using an ultrasonic system and a couplant for a shim that is to be installed in an assembly.

2. Background

Various surfaces may be mated when components are assembled together. In some cases, one or more gaps may be present between the mated surfaces. These gaps may affect the performance, aesthetic, or some other aspect of the object in an undesired manner. Consequently, it may be desirable to substantially fill these gaps using, for example, shims. The process of filling these gaps using shims may be referred to as "shimming."

Some currently available methods for measuring gaps and manufacturing shims, including conventional or virtual measurement based on three-dimensional models, work well when both the mated surfaces are rigid surfaces. However, the shims formed using these types of methods may not have the desired level of accuracy when at least one of the mated surfaces is a flexible surface. For example, when at least one of the mated surfaces is a flexible surface, gaps may change in shape or size. Consequently, the shims needed to fill these gaps may be different from the shims predicted. The shims may need to be reworked, new shims may need to be made, or both. Performing these types of operations may increase the overall time, cost, and effort needed to assemble parts together more than desired. Therefore, it would be desirable to have a method and apparatus that take into account at least some of the issues discussed above, as well as other possible issues.

SUMMARY

In one illustrative example, a method for identifying a geometry for a shim is provided. A first part and a second part are assembled with a couplant positioned between the first part and the second part at a shim location, at which a shim is to be installed, to form an assembly. A pulse of ultrasonic energy is sent into the assembly at each of a set of selected locations along the assembly corresponding to the shim location using an ultrasonic device. A plurality of echoes is detected for each of the set of selected locations using data generated by the ultrasonic device in response to the ultrasonic device receiving reflections of the ultrasonic energy. The geometry for the shim is identified based on the plurality of echoes detected at each selected location of the set of selected locations.

In another illustrative example, a method for generating data for use in identifying a geometry of a shim is provided. A first part and a second part are assembled with a couplant positioned between the first part and the second part to form an assembly. A pulse of ultrasonic energy is sent into the assembly at each of a set of selected locations along the assembly corresponding to the shim location using an ultrasonic device. Reflections of at least a portion of the ultrasonic energy that is reflected at interfaces formed within the assembly are received for each of the set of selected locations back at the ultrasonic device. Data is generated based on the reflections received at the ultrasonic device. The data is sent to a data processor for processing to identify the geometry for the shim that is to be installed between the first part and the second part.

In yet another illustrative example, an apparatus comprises an ultrasonic device and a data processor. The ultrasonic device is positioned over an assembly. The assembly includes a first part, a second part, and a couplant positioned between the first part and the second. The ultrasonic device sends a pulse of ultrasonic energy into the assembly at each of a set of selected locations along the assembly corresponding to a shim location. The ultrasonic device receives reflections of at least a portion of the ultrasonic energy that is reflected at interfaces within the assembly. The ultrasonic device generates data for the reflections received. The data processor receives the data and identifies a geometry for the shim using the data.

The features and functions can be achieved independently in various embodiments of the present disclosure or may be combined in yet other embodiments in which further details can be seen with reference to the following description and drawings.

BRIEF DESCRIPTION OF THE DRAWINGS

The novel features believed characteristic of the illustrative embodiments are set forth in the appended claims. The illustrative embodiments, however, as well as a preferred mode of use, further objectives and features thereof, will best be understood by reference to the following detailed description of an illustrative embodiment of the present disclosure when read in conjunction with the accompanying drawings, wherein:

DETAILED DESCRIPTION

The illustrative embodiments recognize and take into account different considerations. For example, the illustrative embodiments recognize and take into account that it may be desirable to have a method and apparatus for identifying a shim geometry for a shim that is to be installed between two mated surfaces with a desired level of accuracy when at least one of the two mated surfaces is a flexible surface. Further, the illustrative embodiments recognize and take into account that it may be desirable to automate the process of identifying shim geometries for shims to reduce the overall amount of time needed to design, manufacture, and install shims.

Thus, the illustrative embodiments provide a method and apparatus for identifying shim geometries. In one illustrative example, a first part and a second part are assembled with a couplant positioned between the first part and the second part at a shim location to form an assembly. A pulse of ultrasonic energy is sent into the assembly at a set of selected locations along the assembly corresponding to the shim location using an ultrasonic device. A plurality of echoes is detected at each of the set of selected locations using the ultrasonic device. A shim geometry for a shim that is to be installed at the shim location is identified based on the plurality of echoes detected at each selected location of the set of selected locations and the material properties of the couplant. For example, the speed at which an ultrasonic wave travels through the couplant may be used in the identification of the shim geometry for the shim.

Figure 1:
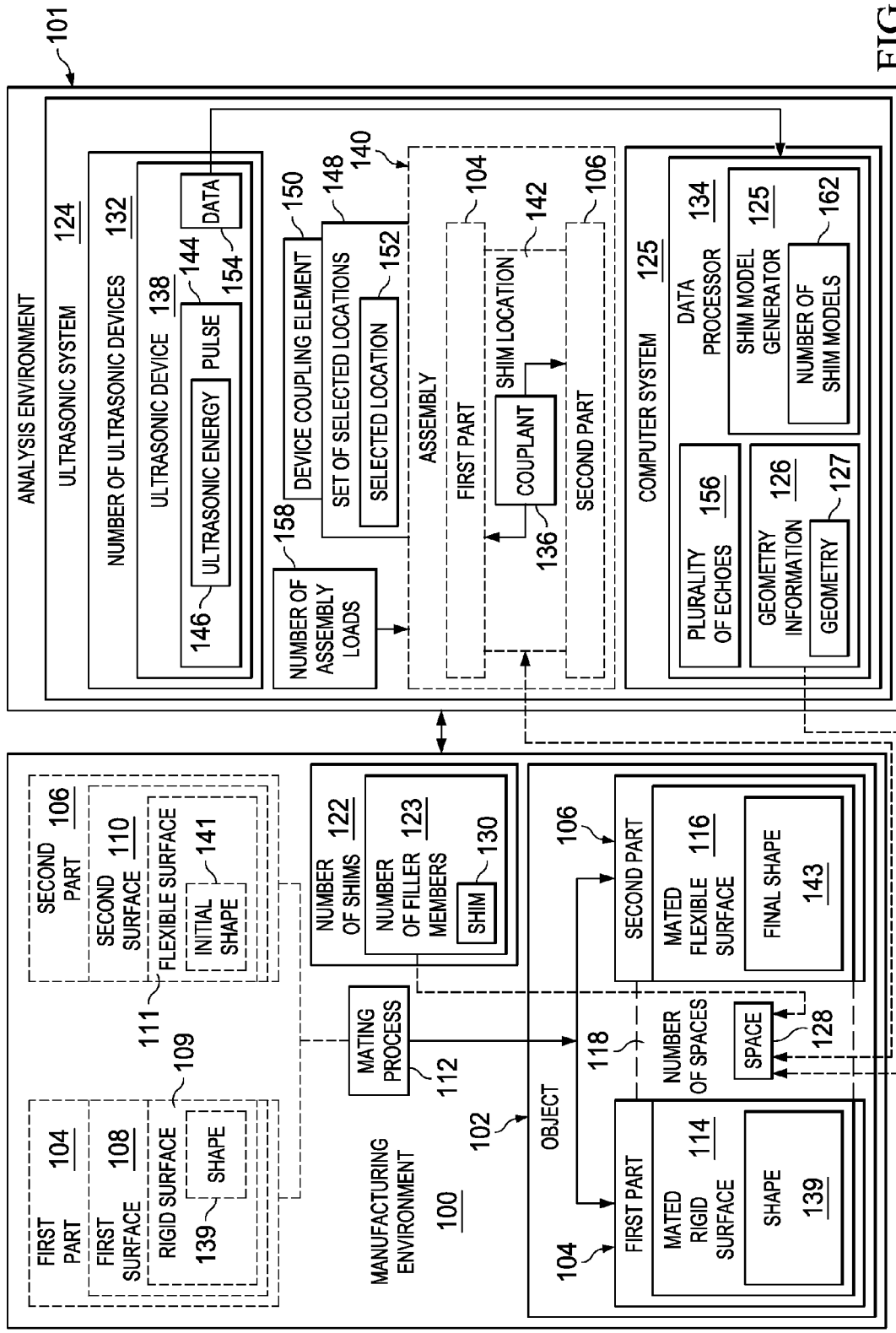
FIG. 1 is an illustration of a manufacturing environment and an analysis environment in the form of a block diagram in accordance with an illustrative embodiment.

Referring now to the figures and, in particular, with reference to FIG. 1, an illustration of a manufacturing environment and an analysis environment is depicted in the form of a block diagram in accordance with an illustrative embodiment. In this illustrative example, manufacturing environment 100 and analysis environment 101 are depicted. Manufacturing environment 100 is an example of an environment in which object 102 may be assembled.

Object 102 may be manufactured using at least first part 104 and second part 106. Any number of other parts may also be used to form object 102. Each of first part 104 and second part 106 may take the form of a single unitary part, a sub-assembly of parts, or an assembly of parts.

First part 104 has first surface 108 and second part 106 has second surface 110. As used herein, a "surface" may be a continuous surface or a discontinuous surface comprised of multiple surfaces.

When object 102 is fully assembled, second part 106 may be attached to first part 104 such that second surface 110 of second part 106 is mated with first surface 108 of first part 104. In particular, first surface 108 of first part 104 and second surface 110 of second part 106 may be mated using mating process 112.

Mating process 112 may include any number of operations configured to physically attach second part 106 to first part 104 such that second surface 110 of second part 106 is mated with first surface 108 of first part 104. For example, without limitation, mating process 112 may include at least one of securing, bonding, mounting, welding, fastening, pinning, stitching, stapling, tying, gluing, or otherwise attaching first part 104 and second part 106 together.

As used herein, the phrase "at least one of," when used with a list of items, means different combinations of one or more of the listed items may be used and only one of the items in the list may be needed. The item may be a particular object, thing, step, operation, process, or category. In other words, "at least one of" means any combination of items or number of items may be used from the list, but not all of the items in the list may be required.

For example, without limitation, "at least one of item A, item B, or item C" may mean item A; item A and item B; item B; item A, item B, and item C; or item B and item C. In some cases, "at least one of item A, item B, or item C" may mean, but is not limited to, two of item A, one of item B, and ten of item C; four of item B and seven of item C; or some other suitable combination.

At least one of first part 104 or second part 106 may be flexible such that the corresponding surface of the component is a flexible surface. In this manner, at least one of first surface 108 or second surface 110 may be a flexible surface. In this manner, a surface, which may be first surface 108, may be mated with a flexible surface, which may be second surface 110, to form a mated surface and a mated flexible surface. In some cases, first surface 108 may be a rigid surface.

As one illustrative example, first part 104 may be rigid such that first surface 108 of first part 104 is also rigid. In particular, first surface 108 may take the form of rigid surface 109. First part 104 may be unable to be bent, deformed, or flexed in a manner outside of selected tolerances. Consequently, the shape of rigid surface 109 may not be changeable outside of selected tolerances.

In contrast, second part 106 is flexible such that second surface 110 of second part 106 is also flexible. In particular, second surface 110 may take the form of flexible surface 111. Second part 106 may be bent, deformed, or flexed without causing any undesired effects to second part 106 or flexible surface 111, such as cracking or tearing. Consequently, the shape of flexible surface 111 may change.

As used herein, a "shape" of a surface, such as first surface 108 or second surface 110, may include the geometry of the surface, the dimensions of the surface, and the morphology of the surface. In particular, the shape of a surface may be the three-dimensional shape of the surface.

Rigid surface 109 and flexible surface 111 may be mated by mating process 112 to form mated rigid surface 114 and mated flexible surface 116, respectively. In particular, once rigid surface 109 and flexible surface 111 have been fully mated, rigid surface 109 may be referred to as mated rigid surface 114 and flexible surface 111 may be referred to as mated flexible surface 116. Rigid surface 109 may have shape 139. After mating process 112, mated flexible surface 116 may have final shape 143 that is different from initial shape 141. However, rigid surface 109 may still have substantially shape 139 after mating process 112.

Number of spaces 118 may be present between mated rigid surface 114 and mated flexible surface 116. As used herein, a "number of" means one or more. In this manner, number of spaces 118 may include one or more spaces. A space in number of spaces 118 may also be referred to as a gap in some illustrative examples. In this manner, number of spaces 118 may also be referred to as a number of gaps.

Number of shims 122 may be used to substantially fill number of spaces 118 within selected tolerances. A shim may be a piece of material or an object configured for filling a space. In some illustrative examples, number of shims 122 may be referred to as number of filler members 123. Depending on the implementation, a shim in number of shims 122 may be fabricated or otherwise manufactured using a material comprised of at least one of plastic, metal, a metal alloy, wood, a composite material, stone, or some other type of material.

In some cases, it may be desirable to manufacture number of shims 122 before mating process 112, in a different location than where mating process 112 is performed, or both to reduce the time, cost, and effort associated with manufacturing object 102. In this illustrative example, ultrasonic system 124 may be used to identify geometry information 126 for each of number of spaces 118 that will be formed between mated rigid surface 114 and mated flexible surface 116.

As one illustrative example, ultrasonic system 124 may be used to identify geometry 127 of space 128 of number of spaces 118. Geometry 127 of space 128 may include at least one of the three-dimensional shape of space 128, three-dimensional geometric dimensions for space 128, or other types of information. Shim 130 may then be manufactured prior to mating process 112 for space 128 based on geometry 127 identified for space 128. Geometry information 126 may include the geometry of each of number of spaces 118.

In this manner, number of shims 122 may be manufactured for number of spaces 118 using geometry information 126 prior to mating process 112. Number of shims 122 may be manufactured using any number of manufacturing processes including, but not limited to, at least one of machining, cutting, bending, hammering, casting, three-dimensional printing, aerosol jet deposition, inkjet deposition, or some other type of forming process.

As depicted, ultrasonic system 124 is located within analysis environment 101. Analysis environment 101 is in a remote location with respect to manufacturing environment 100 in this illustrative example. However, in other illustrative examples, one portion of ultrasonic system 124 may be located within manufacturing environment 100, while another portion of ultrasonic system 124 may be located within analysis environment 101. In still other illustrative examples, ultrasonic system 124 may be entirely located within manufacturing environment 100. In this manner, none, some, or all of analysis environment 101 may be located within manufacturing environment 100, depending on the implementation.

In this illustrative example, ultrasonic system 124 may include number of ultrasonic devices 132, data processor 134, and couplant 136. In other illustrative examples, couplant 136 may be considered separate from ultrasonic system 124. In one illustrative example, number of ultrasonic devices 132 includes a single ultrasonic device. In other illustrative examples, number of ultrasonic devices 132 may include an array of ultrasonic devices. Depending on the implementation, each of number of ultrasonic devices 132 may take the form of, for example, without limitation, an ultrasonic transducer.

Ultrasonic device 138 may be an example of one of number of ultrasonic devices 132. Ultrasonic device 138 may be configured to receive ultrasonic waves and convert these ultrasonic waves into an electrical signal. The electrical signal may be digitized and sent to data processor 134 for processing.

In this illustrative example, data processor 134 may be implemented in software, hardware, firmware, or a combination thereof. When software is used, the operations performed by data processor 134 may be implemented using, for example, without limitation, program code configured to run on a processor unit. When firmware is used, the operations performed by data processor 134 may be implemented using, for example, without limitation, program code and data and stored in persistent memory to run on a processor unit.

When hardware is employed, the hardware may include one or more circuits that operate to perform the operations performed by data processor 134. Depending on the implementation, the hardware may take the form of a circuit system, an integrated circuit, an application-specific integrated circuit (ASIC), a programmable logic device, or some other suitable type of hardware device configured to perform any number of operations.

A programmable logic device may be configured to perform certain operations. The device may be permanently configured to perform these operations or may be reconfigurable. A programmable logic device may take the form of, for example, without limitation, a programmable logic array, programmable array logic, a field programmable logic array, a field programmable gate array, or some other type of programmable hardware device.

In some illustrative examples, the operations and processes performed by data processor 134 may be performed using organic components integrated with inorganic components. In some cases, the operations and processes may be performed by entirely organic components, excluding a human being. As one illustrative example, circuits in organic semiconductors may be used to perform these operations and processes.

In one illustrative example, data processor 134 may be implemented using computer system 125. Computer system 125 may include one or more computers. When computer system 125 includes more than one computer, these computers may be in communication with each other using any number of wired, wireless, optical, or other types of communications links.

The process of identifying geometry 127 for shim 130 may be performed by first assembling first part 104 and second part 106 with couplant 136 positioned between first part 104 and second part 106 at shim location 142 to form assembly 140. Shim location 142 is the location at which shim 130 will need to be installed.

Couplant 136 may take the form of a material that is used to facilitate the transmission of ultrasonic energy across space 128 between first part 104 and second part 106. Couplant 136 may take the form of a thin film of oil or glycerin, a flexible pouch filled with glycerin or water, or some other type of coupling medium. In some cases, couplant 136 may be comprised of a gel material, a rubber material, a film of glycerin, a film of rubber, a fluid, or some other type of material.

Couplant 136 may be comprised of any number of materials that provide couplant 136 with flexibility and enable couplant 136 to maintain sufficient contact with both first part 104 and second part 106. Further, couplant 136 may have one or more material properties that enable couplant 136 to hold its position and maintain sufficient contact with both first part 104 and second part 106 during movement of assembly 140. For example, couplant 136 may have one or more material properties that enable couplant 136 to remain positioned at shim location 142 when the orientation of assembly 140 is changed. These one or more material properties may include, but are not limited to, viscosity and surface tension.

Ultrasonic device 138 may be used to send pulse 144 of ultrasonic energy 146 into assembly 140 at each of set of selected locations 148 along assembly 140 that correspond to shim location 142. More specifically, set of selected locations 148 may substantially overlap with shim location 142.

Set of selected locations 148 may be selected such that geometry 127 may be identified with a desired level of accuracy. For example, set of selected locations 148 may be selected such that the selected locations are evenly distributed over shim location 142. In some cases, set of selected locations 148 may be selected such that the selected locations overlap an area around and within the border of shim location 142. In other illustrative examples, set of selected locations 148 may be selected to include locations at a center of shim location 142 and at the corners of shim location 142. In this manner, set of selected locations 148 may be selected in a number of different ways to provide the desired sampling of shim location 142.

The number of selected locations included in set of selected locations 148 may be determined based on at least one of the type of geometry 127 for shim 130 to be identified, the size of shim 130 to be installed, the desired accuracy with which geometry 127 is to be identified, or some other type of factor. For example, when identifying geometry 127 for shim 130 that is three-dimensional, set of selected locations 148 may be selected to include at least three different locations. Further, the number of selected locations included in set of selected locations 148 may be increased as the size of shim 130 increases. Still further, increasing the number of selected locations in set of selected locations 148 may improve the accuracy with which geometry 127 is identified.

In one illustrative example, device coupling element 150, which may be different from couplant 136, may be used to couple ultrasonic device 138 to assembly 140. Device coupling element 150 may enable ultrasonic energy 146 to travel more easily from ultrasonic device 138 into assembly 140 and may enable the reflections of this ultrasonic energy 146 to travel more easily from assembly 140 to ultrasonic device 138.

As one illustrative example, device coupling element 150 is positioned at selected location 152 at a first side of assembly 140. This first side of the assembly may be at an outer surface of second part 106. Selected location 152 is an example of one of set of selected locations 148.

Ultrasonic device 138 is then positioned over device coupling element 150 and in contact with device coupling element 150 relative to selected location 152. Ultrasonic device 138 sends pulse 144 of ultrasonic energy 146 into assembly 140 at selected location 152.

As pulse 144 propagates through assembly 140, a portion of ultrasonic energy 146 may be reflected back towards ultrasonic device 138 each time that pulse 144 encounters a different interface in assembly 140. For example, a reflection of at least a portion of ultrasonic energy 146 that is reflected at an interface between device coupling element 150 and second part 106 may be received at ultrasonic device 138. Similarly, a reflection of at least a portion of ultrasonic energy 146 that is reflected at an interface between couplant 136 and first part 104 may be received at ultrasonic device 138. Further, a reflection of at least a portion of ultrasonic energy 146 that is reflected at an interface between couplant 136 and second part 106 may be received at ultrasonic device 138.

Ultrasonic device 138 converts ultrasonic waves received at ultrasonic device 138 into an electrical signal that is digitized to form data 154. Data 154 is sent to data processor 134 for processing. Data processor 134 may detect peaks in the electrical signal that represent the reflections of ultrasonic energy 146 at the different interfaces of assembly 140. These peaks may be referred to as echoes. Plurality of echoes 156 may be identified for each of set of selected locations 148.

Data processor 134 uses plurality of echoes 156 detected for each of set of selected locations 148 and the time at which each of plurality of echoes 156 was detected to identify geometry 127 for shim 130. In this manner, geometry 127 for shim 130 may be quickly and easily identified.

In some cases, prior to sending pulse 144 into assembly 140, number of assembly loads 158 may be applied to assembly 140. Number of assembly loads 158 may be applied to assembly 140 to simulate a number of factors related to mating process 112 that may cause initial shape 141 of second part 106 to change.

The number of factors may include at least one of, for example, without limitation, the operations involved in mating process 112, the sequence of operations performed in mating process 112, a number of forces applied to flexible surface 111 during mating process 112, loads applied to flexible surface 111 during the formation and shaping of flexible surface 111, a number of boundary conditions, gravity, or some other factor. Still other factors may include, but are not limited to, attachment points, contact between rigid surface 109 and flexible surface 111 during and after mating process 112, the orientation of first part 104, second part 106, or both. In this manner, any factor that may affect the shape of flexible surface 111 before, during, and/or after mating process 112 may be considered when applying number of assembly loads 158 to assembly 140.

In some cases, different scenarios for number of assembly loads 158 may be used to identify different geometries for shim 130. As one illustrative example, three different assembly loads may be identified for three different scenarios. Each of these three assembly loads may correspond to a different stage of assembly, which may occur prior to or after the installation of shim 130.

A first geometry for shim 130 may be identified after applying the first assembly load to assembly 140. Next, a second geometry for shim 130 may be identified after applying the second assembly load to assembly 140. Then, a third geometry for shim 130 may be identified after applying the third assembly load to assembly 140. These different geometries may be averaged or processed in some other manner to identify a final geometry 127 for shim 130. In some cases, the differences between the various geometries may be used to evaluate how the space 128 between first part 104 and second part 106 and shim 130 are affected by these assembly loads.

Shim model generator 160 in data processor 134 may then generate number of shim models 162 based on geometry information 126. Number of shims 122 may then be manufactured based on number of shim models 162 such that number of shims 122 can be used to substantially fill number of spaces 118 within selected tolerances. By manufacturing number of shims 122 based on geometry information 126 identified by ultrasonic system 124, filling number of spaces 118 may be performed more quickly and accurately as compared to manufacturing number of shims 122 based on manual measurements of number of spaces 118. As a result, the amount of rework that may be needed during shimming and the number of new shims that may be needed during shimming may be reduced.

The illustration of manufacturing environment 100, analysis environment 101, object 102, and ultrasonic system 124 in FIG. 1 is not meant to imply physical or architectural limitations to the manner in which an illustrative embodiment may be implemented. Other components in addition to or in place of the ones illustrated may be used. Some components may be optional. Also, the blocks are presented to illustrate some functional components. One or more of these blocks may be combined, divided, or combined and divided into different blocks when implemented in an illustrative embodiment.

For example, in some cases, device coupling element 150 may be associated with ultrasonic device 138. Depending on the implementation, device coupling element 150 may be attached to ultrasonic device 138 or part of ultrasonic device 138. In some illustrative examples, device coupling element 150 may be a material that makes up the surface of ultrasonic device 138 that is to come into contact with parts. In other illustrative examples, device coupling element 150 may be a coating on the surface of ultrasonic device 138 that is to come into contact with parts. In some illustrative examples, air may be used in the place of device coupling element 150.

In some illustrative examples, plurality of echoes 156 may be detected and identified by ultrasonic device 138. Data about plurality of echoes 156 may then be sent to data processor 134 for processing.

Figure 2:
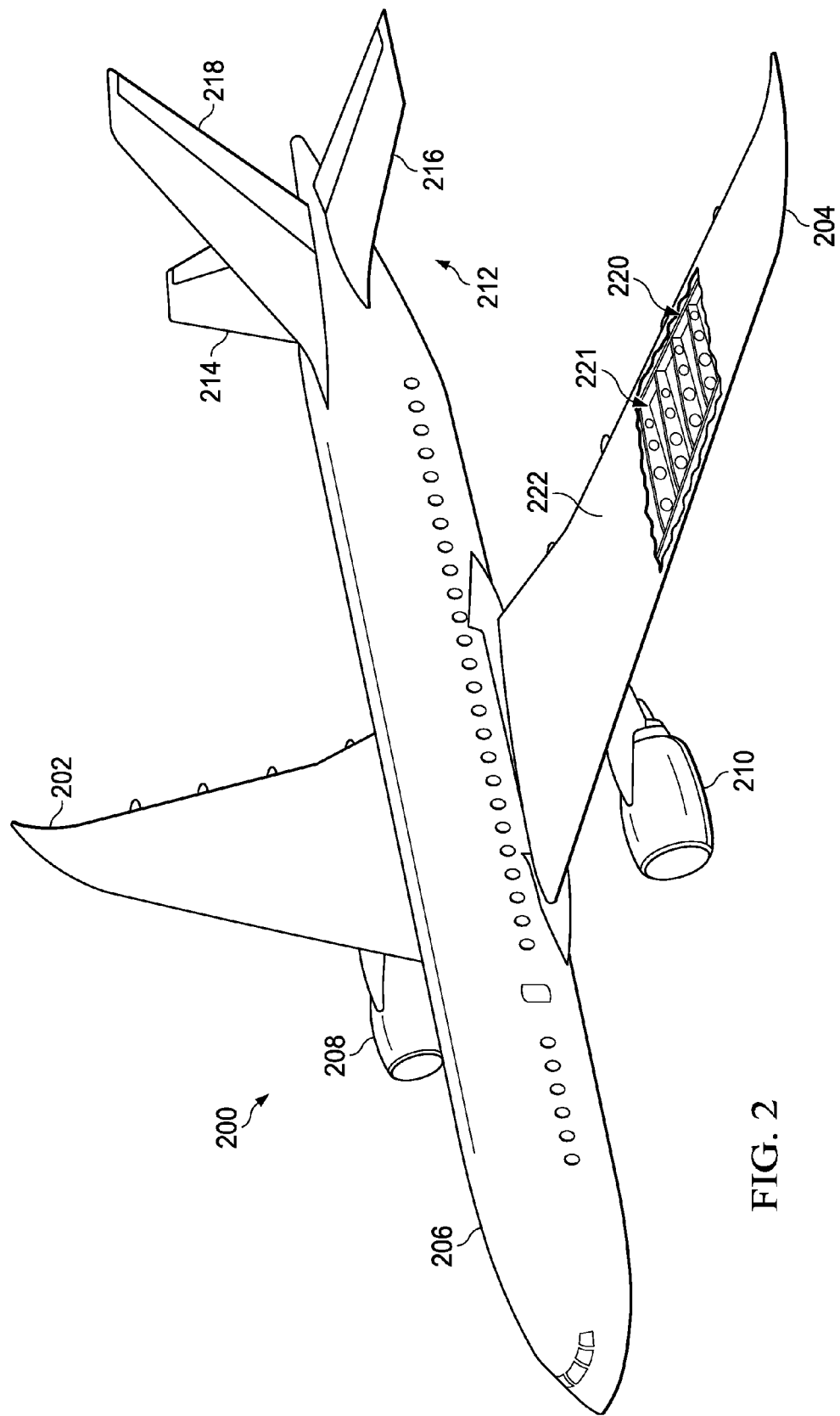
FIG. 2 is an illustration of an aircraft in accordance with an illustrative embodiment.

With reference now to FIG. 2, an illustration of an aircraft is depicted in accordance with an illustrative embodiment. In this illustrative example, aircraft 200 has wing 202 and wing 204 attached to body 206. Aircraft 200 includes engine 208 attached to wing 202 and engine 210 attached to wing 204. Body 206 has tail section 212. Horizontal stabilizer 214, horizontal stabilizer 216, and vertical stabilizer 218 are attached to tail section 212 of body 206.

Wing 204 of aircraft 200 is an example of one implementation for object 102 in FIG. 1. A portion of wing 204 has been cut away to expose a portion of wing structure 220 of wing 204. Wing structure 220 may be referred to as a wing box in other illustrative examples.

Wing structure 220 includes rib assembly 221. Panel 222 is attached to rib assembly 221. Panel 222 may also be referred to as a skin or a wing skin. Depending on the implementation, panel 222 may have one or more stringers attached to panel 222. Rib assembly 221 is an example of one implementation of first part 104 in FIG. 1. Panel 222 is an example of one implementation of second part 106 in FIG. 1.

Figure 3:
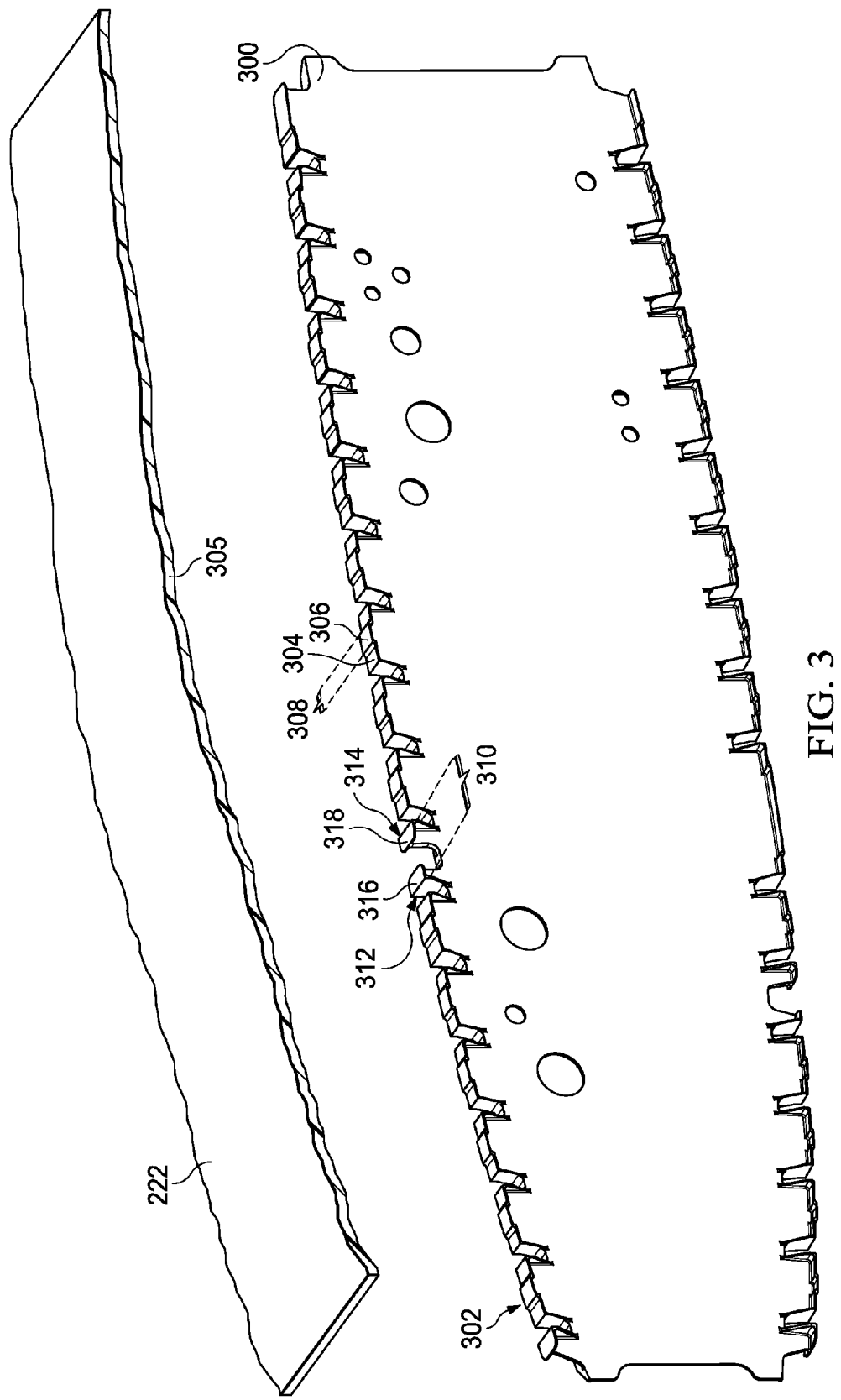
FIG. 3 is an isometric view of a rib in a rib assembly in accordance with an illustrative embodiment.

With reference now to FIG. 3, an isometric view of a rib in rib assembly 221 in FIG. 2 is depicted in accordance with an illustrative embodiment. In this illustrative example, rib 300 is an example of one of the plurality of ribs that make up rib assembly 221 in FIG. 2.

As depicted, rib 300 has plurality of shear ties 302 that form a rigid surface for rib 300. This rigid surface is a discontinuous rigid surface. In particular, each of plurality of shear ties 302 has at least one rigid surface that forms the discontinuous rigid surface for rib 300.

Shear tie 304 is an example of one of plurality of shear ties 302. As depicted, shear tie 304 has surface 306, which is rigid. Panel 222 from FIG. 2 may have flexible surface 305. Panel 222 may be attached to shear tie 304 to mate a portion of flexible surface 305 of panel 222 to surface 306 of shear tie 304 at a selected portion of shear tie 304. This selected portion of shear tie 304 may be referred to as cap 308 of shear tie 304. In one illustrative example, panel 222 may be tacked to cap 308 to mate flexible surface 305 of panel 222 with surface 306.

Shear tie 310 is another example of one of plurality of shear ties 302. Shear tie 310 includes flange 312 and flange 314. Flange 312 has surface 316 and flange 314 has surface 318. Both surface 316 of flange 312 and surface 318 of flange 314 are rigid. Panel 222 may be attached to flange 312 and flange 314 to mate panel 222 to surface 316 and surface 318, respectively. In particular, panel 222 may be tacked to flange 312 and flange 314 to mate panel 222 to surface 316 and surface 318, respectively.

In this manner, flexible surface 305 of panel 222 may be mated to each of plurality of shear ties 302. Depending on the implementation, flexible surface 305 may be fastened to the surfaces of plurality of shear ties 302 using any number of fastener devices or elements. For example, at least one of tacks, pins, nails, screws, bolts, or some other type of fastener device. Fastening flexible surface 305 to these surfaces, as well as gravity and other factors, may cause the cross-sectional shape of flexible surface 305 to change.

An ultrasonic system, such as ultrasonic system 124 in FIG. 1, may be used to identify the geometries of the shims that may be needed to substantially fill any undesired spaces between flexible surface 305 and the surfaces of plurality of shear ties 302. These undesired spaces may need to be filled to maintain the desired or selected aerodynamic profile for wing 204. If these spaces are not substantially filled within selected tolerances, the loads applied to panel 222 during flight of aircraft 200 may cause panel 222 to deform in an undesired manner at the locations of these spaces, which may, in turn, change the aerodynamic profile of wing 204 in an undesired manner.

One or more couplants, such as couplant 136 described in FIG. 1 may be used with an ultrasonic device, such as ultrasonic device 138 described in FIG. 1, to identify the geometry of the shims needed to fill the spaces between the surfaces of plurality of shear ties 302 and panel 222. In one illustrative example, a single couplant may be placed over all of the surfaces of plurality of shear ties 302. Panel 222 may then be placed over the couplant and ultrasonic testing performed to identify the geometries of the shims that are needed. In another illustrative example, a different couplant may be placed over each surface of plurality of shear ties 302. Panel 222 may then be placed over these different couplants and ultrasonic testing performed.

In still other illustrative examples, one couplant may be placed over a single surface of plurality of shear ties 302 and panel 222, then placed over the couplant. Ultrasonic testing may then be performed. This process may then be repeated for each remaining surface of plurality of shear ties 302.

Figure 4:
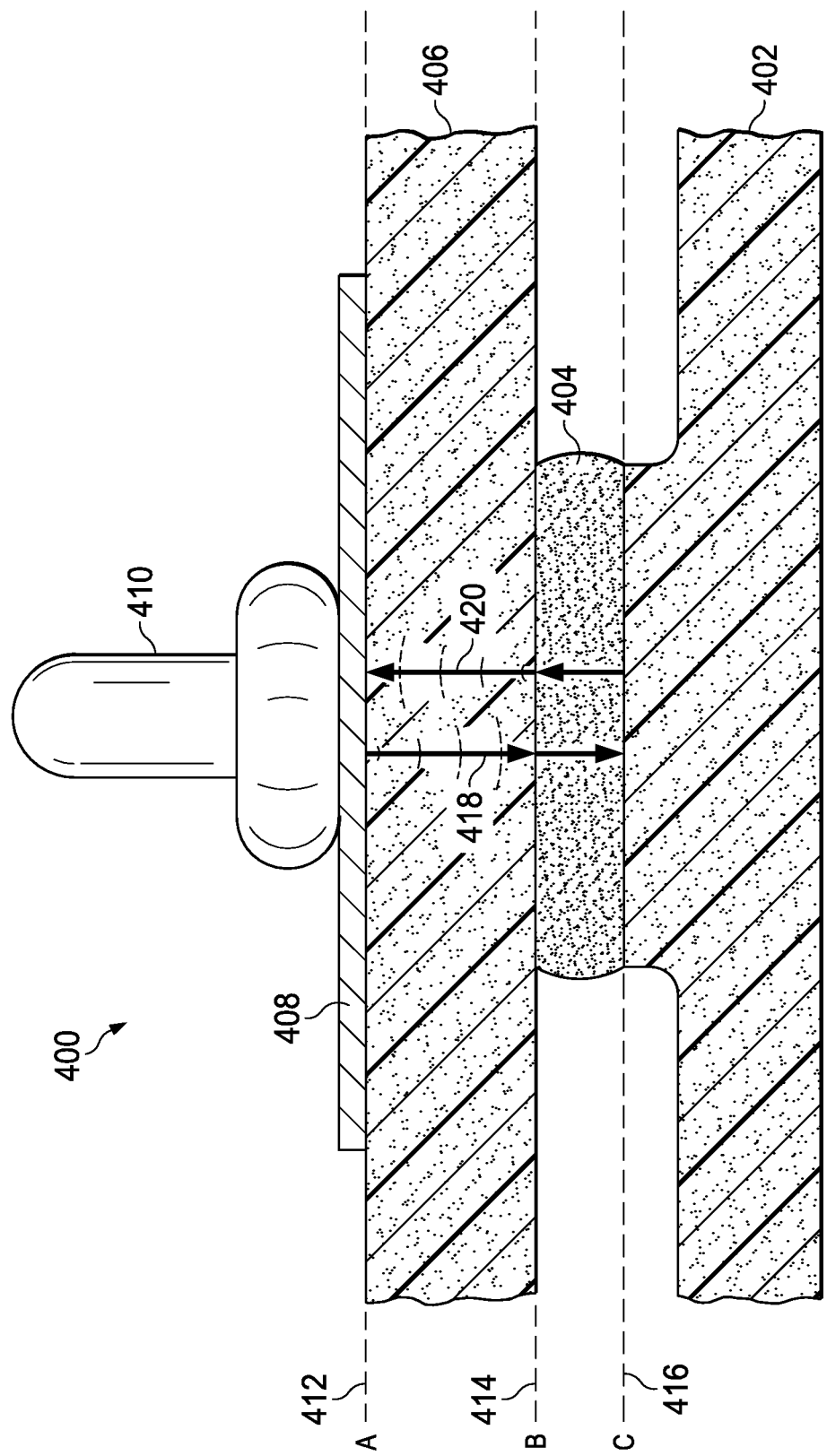
FIG. 4 is an illustration of an assembly and an ultrasonic device in accordance with an illustrative embodiment.

With reference now to FIG. 4, an illustration of an ultrasonic device positioned over an assembly is depicted in accordance with an illustrative embodiment. In this illustrative example, assembly 400 includes first part 402, couplant 404, and second part 406. First part 402, couplant 404, and second part 406 may be examples of implementations for first part 104, couplant 136, and second part 106, respectively, in FIG. 1.

In this illustrative example, device coupling element 408 is positioned over second part 406 and ultrasonic device 410 is positioned over device coupling element 408. Device coupling element 408 and ultrasonic device 410 may be examples of implementations for device coupling element 150 and ultrasonic device 138, respectively, in FIG. 1.

Interface 412 is formed between device coupling element 408 and second part 406. Interface 414 is formed between second part 406 and couplant 404. Interface 416 is formed between couplant 404 and first part 402.

Ultrasonic device 410 sends pulse 418 of ultrasonic energy into assembly 400. Reflections 420 of ultrasonic energy being reflected at each of interface 412, 414, and 416 may be received back at ultrasonic device 410.

Figure 5:
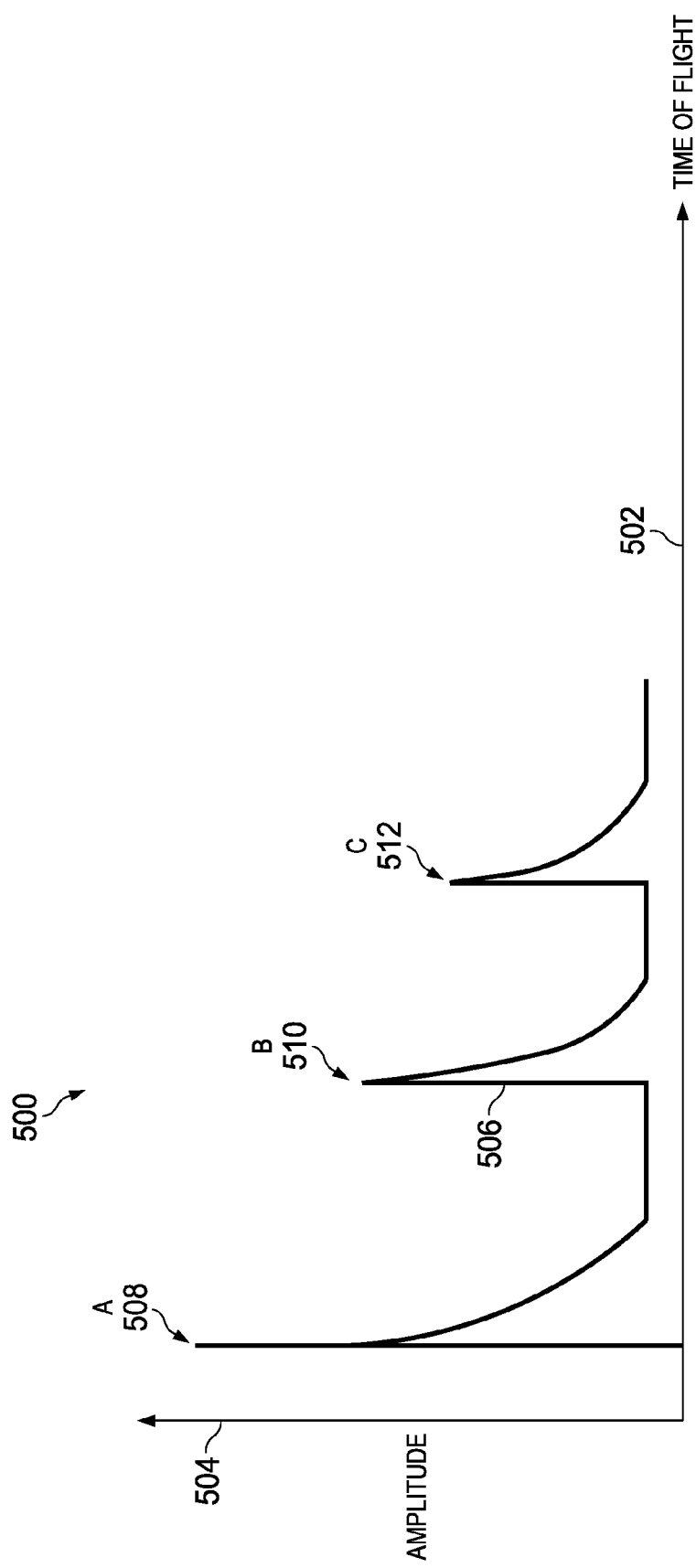
FIG. 5 is an illustration of a graph of an electrical signal generated by an ultrasonic device in accordance with an illustrative embodiment.

With reference now to FIG. 5, an illustration of a graph of an electrical signal generated by ultrasonic device 410 in FIG. 4 is depicted in accordance with an illustrative embodiment. In this illustrative example, graph 500 includes horizontal axis 502, vertical axis 504, and curve 506.

Curve 506 represents an electrical signal generated by ultrasonic device 410 in FIG. 4 in response to pulse 418 being sent into assembly 400. Horizontal axis 502 may be time. Vertical axis 504 may be the amplitude of the electrical signal.

Peak 508, peak 510, and peak 512 may represent the receiving of the reflections of ultrasonic energy that is reflected at interface 412, interface 414, and interface 416, respectively, in FIG. 4. The time intervals between each of these peaks may be used to determine a distance between each of these interfaces, which may, in turn, be used to identify the distance between first part 402 and second part 406 in FIG. 4.

For example, the time interval between the time at which peak 508 is detected and the time at which peak 510 is detected may be a measure of the thickness of second part 406 in FIG. 4. The time interval between the time at which peak 510 is detected and the time at which peak 512 is detected may be a measure of the distance between first part 402 and second part 406 in FIG. 4.

The distance between first part 402 and second part 406 may be computed as follows:

$$d_{BC} = \frac{v(t_C - t_B)}{2}$$

Where $d_{BC}$ is the distance between interface 414 and interface 416 in FIG. 4, $t_C$ is the time at which peak 512 is detected, $t_B$ is the time at which peak 510 is detected, and $v$ is the speed at which the ultrasonic wave travels through the couplant 404 in FIG. 4.

Figure 6:
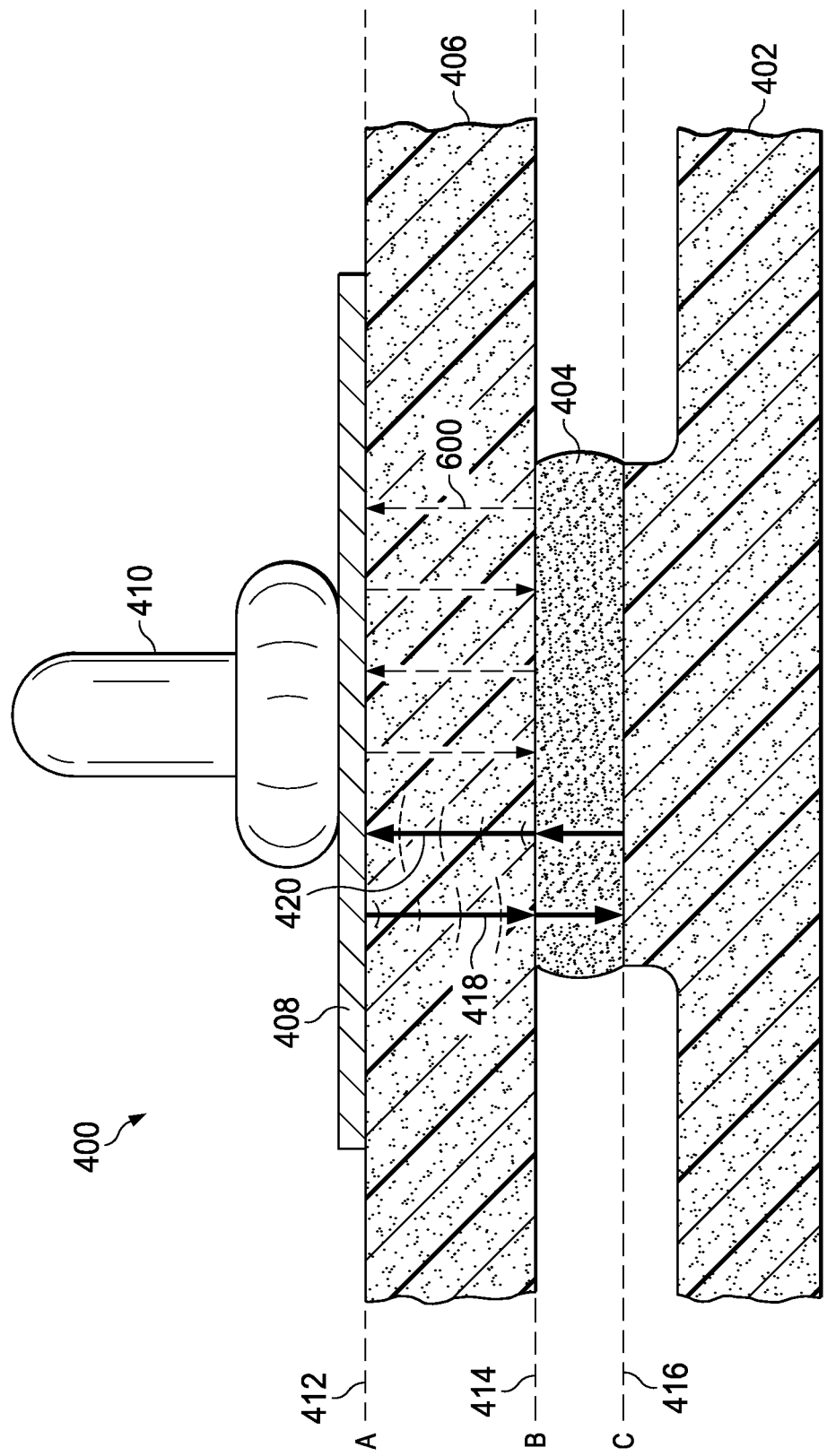
FIG. 6 is an illustration of an assembly and an ultrasonic device in accordance with an illustrative embodiment.

With reference now to FIG. 6, an illustration of assembly 400 and ultrasonic device 410 from FIG. 4 is depicted in accordance with an illustrative embodiment. In some cases, additional reflections 600 may be detected at ultrasonic device 410 that are not the reflections of ultrasonic energy at any of interface 412, interface 414, or interface 416.

Additional reflections 600 may be detected as peaks in the electrical signal generated by ultrasonic device 410. These types of reflections may need to be taken into account when processing the data received from ultrasonic device 410. Additional reflections 600 may occur when the ultrasonic wave speed in second part 406 is much higher than the ultrasonic wave speed in couplant 404, when the thickness of second part 406 is much smaller than the distance between first part 402 and second part 406, or when both of these conditions are present.

The illustrations in FIGS. 2-6 are not meant to imply physical or architectural limitations to the manner in which an illustrative embodiment may be implemented. Other components in addition to or in place of the ones illustrated may be used. Some components may be optional.

The different components shown in FIGS. 2-6 may be illustrative examples of how components shown in block form in FIG. 1 can be implemented as physical structures. Additionally, some of the components in FIGS. 2-6 may be combined with components in FIG. 1, used with components in FIG. 1, or a combination of the two.

Figure 7:
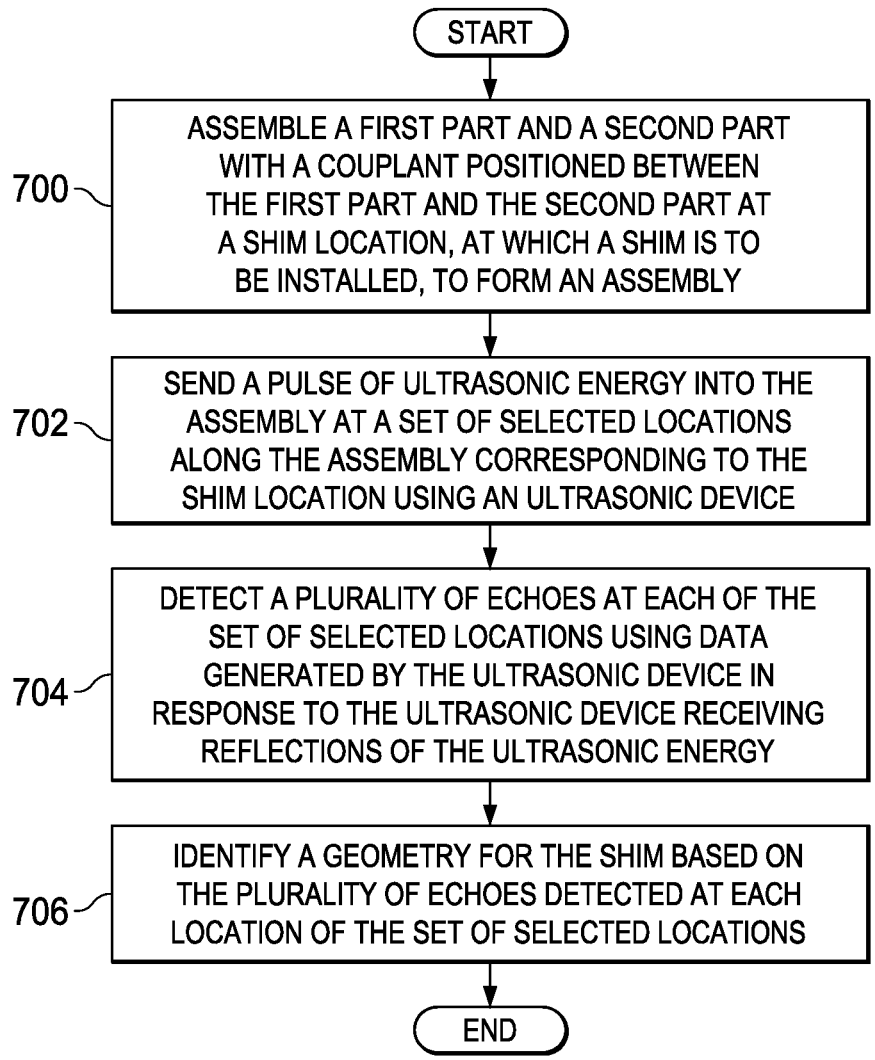
FIG. 7 is an illustration of a process for identifying a shim geometry for a shim in the form of a flowchart in accordance with an illustrative embodiment.

With reference now to FIG. 7, an illustration of a process for identifying a geometry for a shim is depicted in the form of a flowchart in accordance with an illustrative embodiment. The process illustrated in FIG. 7 may be used to identify, for example, geometry 127 for shim 130 in FIG. 1.

The process may begin by assembling a first part and a second part with a couplant positioned between the first part and the second part at a shim location, at which a shim is to be installed, to form an assembly (operation 700). Next, a pulse of ultrasonic energy may be sent into the assembly at a set of selected locations along the assembly corresponding to the shim location using an ultrasonic device (operation 702).

In operation 702, the ultrasonic device may be positioned at a selected side of the assembly such that the pulse of ultrasonic energy enters the assembly through the first part or through the second part. In this illustrative example, the selected side may be the exposed side of the second part opposite the side of the second part that is in contact with the couplant. In other illustrative examples, the selected side may be the exposed side of the first part opposite the side of the first part that is in contact with the couplant.

Thereafter, a plurality of echoes may be detected for each of the set of selected locations using data generated by the ultrasonic device in response to the ultrasonic device receiving reflections of the ultrasonic energy (operation 704). Then, a geometry for a shim that is to be installed at the shim location may be identified based on the plurality of echoes detected at each selected location of the set of selected locations (operation 706), with the process terminating thereafter.

Figure 8:
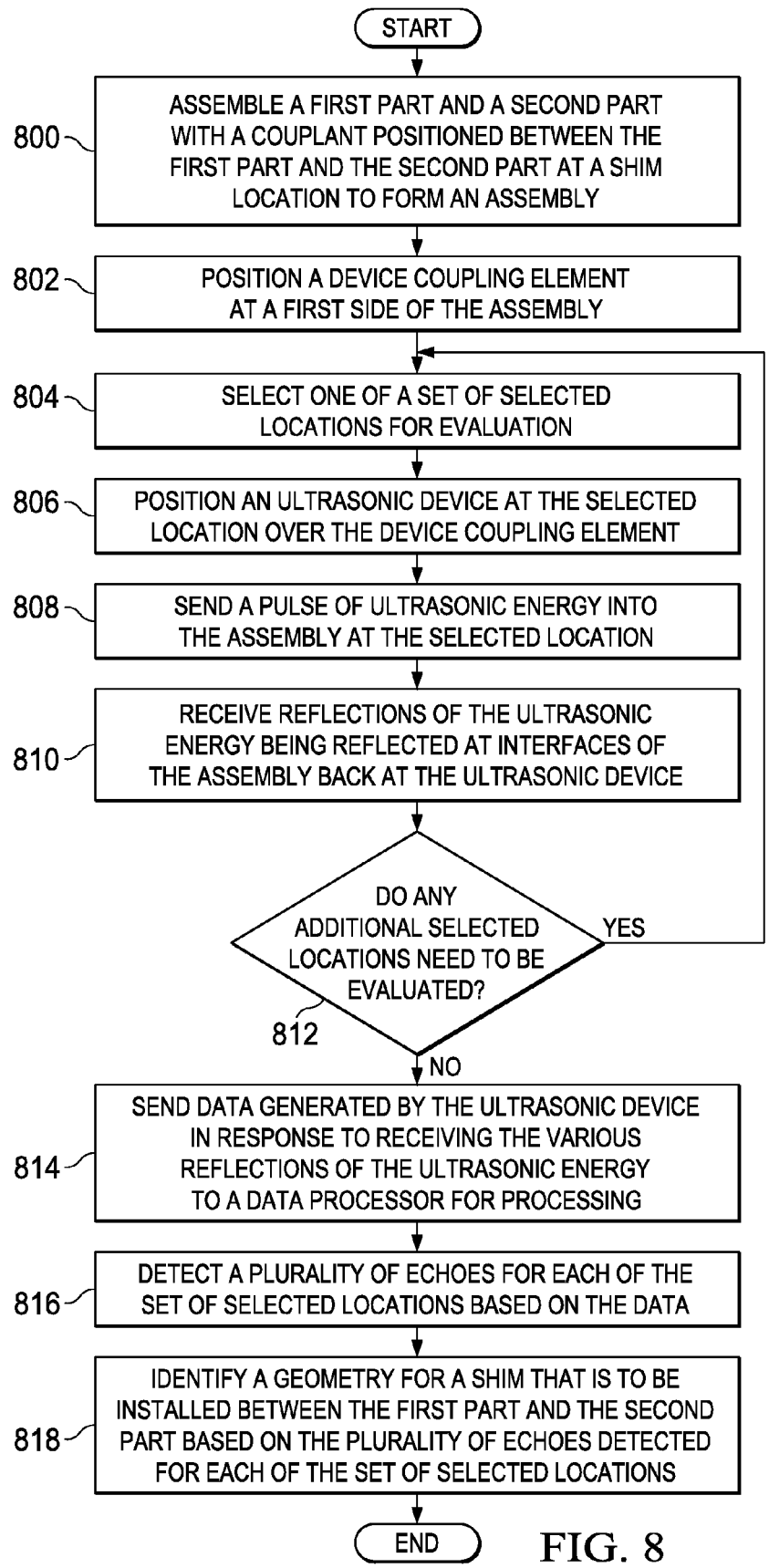
FIG. 8 is an illustration of a process for identifying a shim geometry for a shim in the form of a flowchart in accordance with an illustrative embodiment.

With reference now to FIG. 8, an illustration of a process for identifying a geometry for a shim is depicted in the form of a flowchart in accordance with an illustrative embodiment. The process illustrated in FIG. 8 may be used to identify, for example, geometry 127 for shim 130 in FIG. 1.

The process may begin by assembling a first part and a second part with a couplant positioned between the first part and the second part at a shim location to form an assembly (operation 800). Next, a device coupling element may be positioned at a first side of the assembly (operation 802).

One of a set of selected locations may be selected for evaluation (operation 804). An ultrasonic device may then be positioned at the selected location over the device coupling element (operation 806). A pulse of ultrasonic energy is sent into the assembly at the selected location (operation 808).

Thereafter, reflections of the ultrasonic energy being reflected at interfaces of the assembly are received back at the ultrasonic device (operation 810). A determination may then be made as to whether any additional selected locations need to be evaluated (operation 812). If additional selected locations need to be evaluated, the process returns to operation 804 as described above.

Otherwise, data generated by the ultrasonic device in response to receiving the various reflections of the ultrasonic energy is sent to a data processor for processing (operation 814). A plurality of echoes are detected for each of the set of selected locations based on the data (operation 816). A geometry for a shim that is to be installed between the first part and the second part is identified based on the plurality of echoes detected for each of the set of selected locations (operation 818), with the process terminating thereafter.

The flowcharts and block diagrams in the different depicted embodiments illustrate the architecture, functionality, and operation of some possible implementations of apparatuses and methods in an illustrative embodiment. In this regard, each block in the flowcharts or block diagrams may represent a module, a segment, a function, and/or a portion of an operation or step.

In some alternative implementations of an illustrative embodiment, the function or functions noted in the blocks may occur out of the order noted in the figures. For example, in some cases, two blocks shown in succession may be executed substantially concurrently, or the blocks may sometimes be performed in the reverse order, depending upon the functionality involved. Also, other blocks may be added in addition to the illustrated blocks in a flowchart or block diagram.

Figure 9:
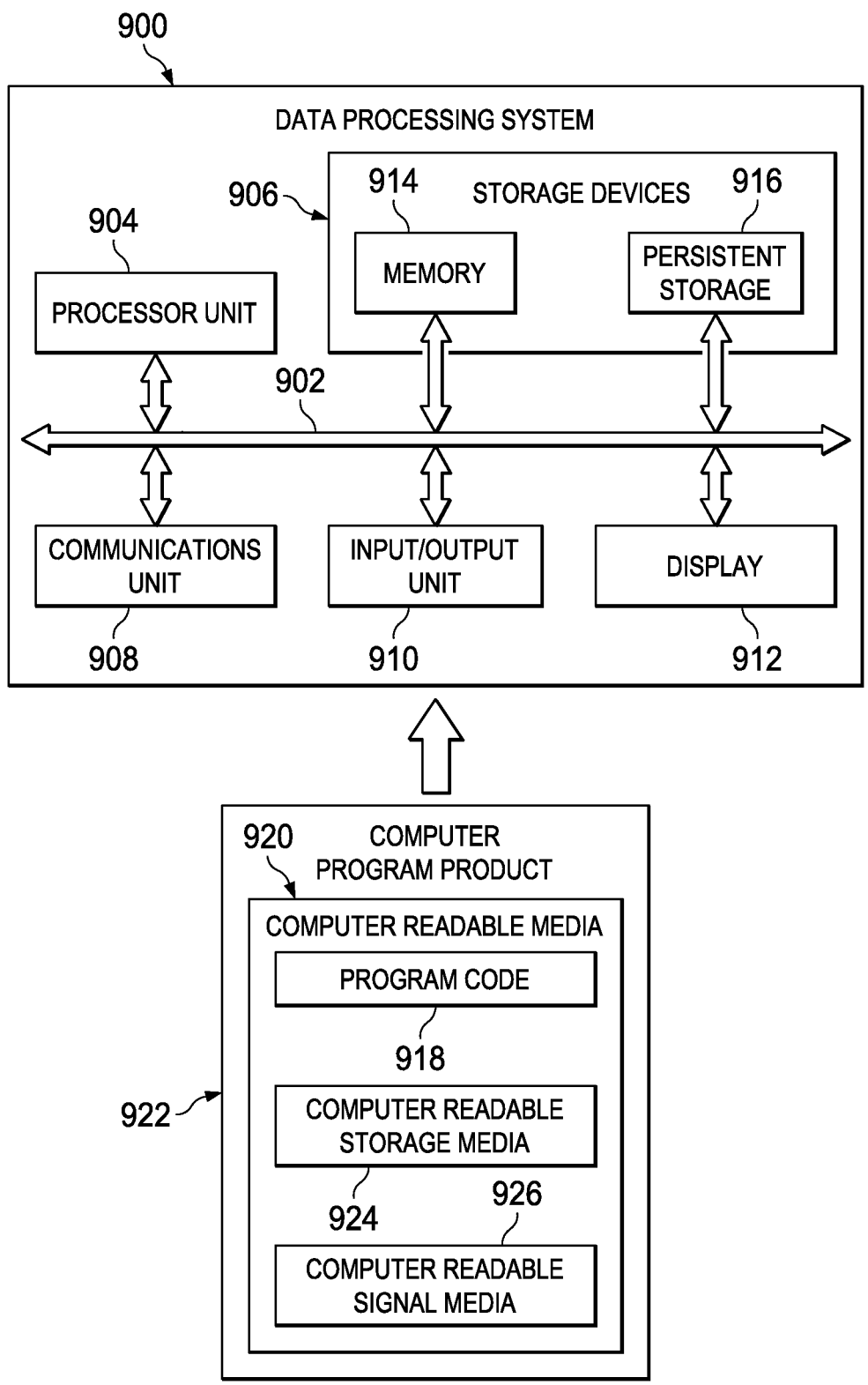
FIG. 9 is an illustration of a data processing system in the form of a block diagram in accordance with an illustrative embodiment.

Turning now to FIG. 9, an illustration of a data processing system in the form of a block diagram is depicted in accordance with an illustrative embodiment. Data processing system 900 may be used to implement computer system 125 in FIG. 1. As depicted, data processing system 900 includes communications framework 902, which provides communications between processor unit 904, storage devices 906, communications unit 908, input/output unit 910, and display 912. In some cases, communications framework 902 may be implemented as a bus system.

Processor unit 904 is configured to execute instructions for software to perform a number of operations. Processor unit 904 may comprise a number of processors, a multi-processor core, and/or some other type of processor, depending on the implementation. In some cases, processor unit 904 may take the form of a hardware unit, such as a circuit system, an application-specific integrated circuit (ASIC), a programmable logic device, or some other suitable type of hardware unit.

Instructions for the operating system, applications, and/or programs run by processor unit 904 may be located in storage devices 906. Storage devices 906 may be in communication with processor unit 904 through communications framework 902. As used herein, a storage device, also referred to as a computer readable storage device, is any piece of hardware capable of storing information on a temporary and/or permanent basis. This information may include, but is not limited to, data, program code, and/or other information.

Memory 914 and persistent storage 916 are examples of storage devices 906. Memory 914 may take the form of, for example, a random access memory or some type of volatile or non-volatile storage device. Persistent storage 916 may comprise any number of components or devices. For example, persistent storage 916 may comprise a hard drive, a flash memory, a rewritable optical disk, a rewritable magnetic tape, or some combination of the above. The media used by persistent storage 916 may or may not be removable.

Communications unit 908 allows data processing system 900 to communicate with other data processing systems and/or devices. Communications unit 908 may provide communications using physical and/or wireless communications links.

Input/output unit 910 allows input to be received from and output to be sent to other devices connected to data processing system 900. For example, input/output unit 910 may allow user input to be received through a keyboard, a mouse, and/or some other type of input device. As another example, input/output unit 910 may allow output to be sent to a printer connected to data processing system 900.

Display 912 is configured to display information to a user. Display 912 may comprise, for example, without limitation, a monitor, a touch screen, a laser display, a holographic display, a virtual display device, and/or some other type of display device.

In this illustrative example, the processes of the different illustrative embodiments may be performed by processor unit 904 using computer-implemented instructions. These instructions may be referred to as program code, computer usable program code, or computer readable program code and may be read and executed by one or more processors in processor unit 904.

In these examples, program code 918 is located in a functional form on computer readable media 920, which is selectively removable, and may be loaded onto or transferred to data processing system 900 for execution by processor unit 904. Program code 918 and computer readable media 920 together form computer program product 922. In this illustrative example, computer readable media 920 may be computer readable storage media 924 or computer readable signal media 926.

Computer readable storage media 924 is a physical or tangible storage device used to store program code 918 rather than a medium that propagates or transmits program code 918. Computer readable storage media 924 may be, for example, without limitation, an optical or magnetic disk or a persistent storage device that is connected to data processing system 900.

Alternatively, program code 918 may be transferred to data processing system 900 using computer readable signal media 926. Computer readable signal media 926 may be, for example, a propagated data signal containing program code 918. This data signal may be an electromagnetic signal, an optical signal, and/or some other type of signal that can be transmitted over physical and/or wireless communications links.

The illustration of data processing system 900 in FIG. 9 is not meant to provide architectural limitations to the manner in which the illustrative embodiments may be implemented. The different illustrative embodiments may be implemented in a data processing system that includes components in addition to or in place of those illustrated for data processing system 900. Further, components shown in FIG. 9 may be varied from the illustrative examples shown.

Figure 10:
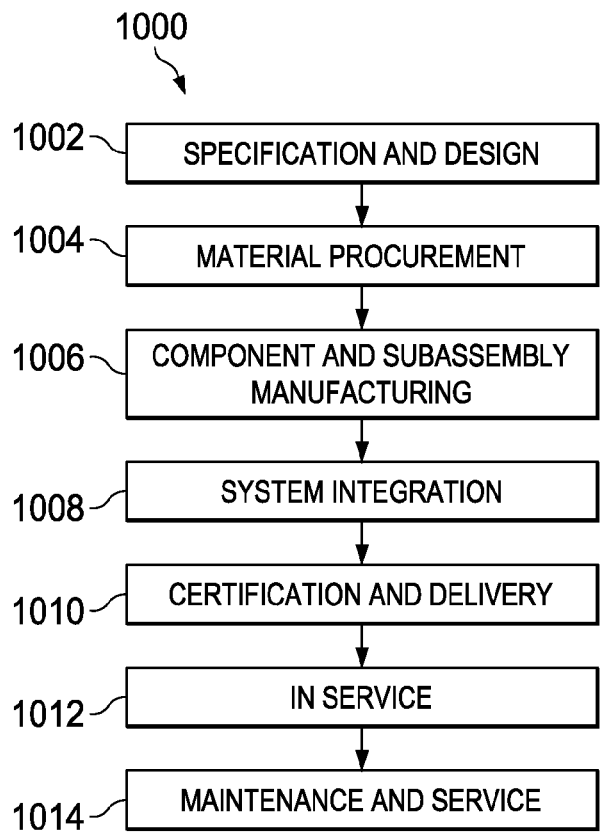
FIG. 10 is an illustration of an aircraft manufacturing and service method in the form of a block diagram in accordance with an illustrative embodiment.
Figure 11:
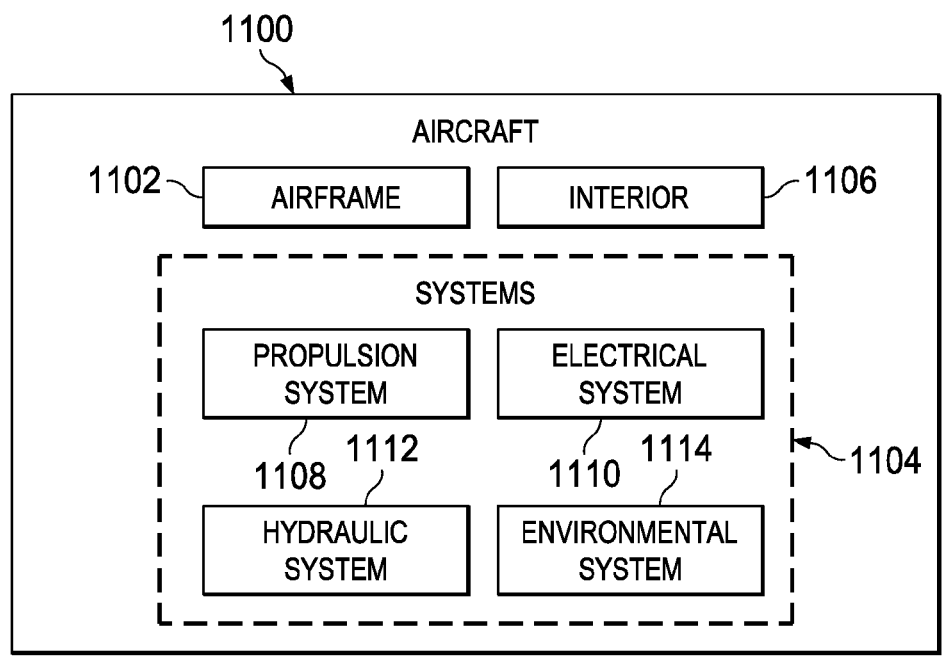
FIG. 11 is an illustration of an aircraft in the form of a block diagram in accordance with an illustrative embodiment.

Illustrative embodiments of the disclosure may be described in the context of aircraft manufacturing and service method 1000 as shown in FIG. 10 and aircraft 1100 as shown in FIG. 11. Turning first to FIG. 10, an illustration of an aircraft manufacturing and service method is depicted in accordance with an illustrative embodiment. During pre-production, aircraft manufacturing and service method 1000 may include specification and design 1002 of aircraft 1100 in FIG. 11 and material procurement 1004.

During production, component and subassembly manufacturing 1006 and system integration 1008 of aircraft 1100 in FIG. 11 takes place. Thereafter, aircraft 1100 in FIG. 11 may go through certification and delivery 1010 in order to be placed in service 1012. While in service 1012 by a customer, aircraft 1100 in FIG. 11 is scheduled for routine maintenance and service 1014, which may include modification, reconfiguration, refurbishment, and other maintenance or service.

Each of the processes of aircraft manufacturing and service method 1000 may be performed or carried out by a system integrator, a third party, and/or an operator. In these examples, the operator may be a customer. For the purposes of this description, a system integrator may include, without limitation, any number of aircraft manufacturers and major-system subcontractors; a third party may include, without limitation, any number of vendors, subcontractors, and suppliers; and an operator may be an airline, a leasing company, a military entity, a service organization, and so on.

With reference now to FIG. 11, an illustration of an aircraft is depicted in which an illustrative embodiment may be implemented. In this example, aircraft 1100 is produced by aircraft manufacturing and service method 1000 in FIG. 10 and may include airframe 1102 with plurality of systems 1104 and interior 1106. Examples of systems 1104 include one or more of propulsion system 1108, electrical system 1110, hydraulic system 1112, and environmental system 1114. Any number of other systems may be included. Although an aerospace example is shown, different illustrative embodiments may be applied to other industries, such as the automotive industry.

Apparatuses and methods embodied herein may be employed during at least one of the stages of aircraft manufacturing and service method 1000 in FIG. 10. In one illustrative example, components or subassemblies produced in component and subassembly manufacturing 1006 in FIG. 10 may be fabricated or manufactured in a manner similar to components or subassemblies produced while aircraft 1100 is in service 1012 in FIG. 10. As yet another example, one or more apparatus embodiments, method embodiments, or a combination thereof may be utilized during production stages, such as component and subassembly manufacturing 1006 and system integration 1008 in FIG. 10. One or more apparatus embodiments, method embodiments, or a combination thereof may be utilized while aircraft 1100 is in service 1012 and/or during maintenance and service 1014 in FIG. 10. The use of a number of the different illustrative embodiments may substantially expedite the assembly of and/or reduce the cost of aircraft 1100.

The description of the different illustrative embodiments has been presented for purposes of illustration and description, and is not intended to be exhaustive or limited to the embodiments in the form disclosed. Many modifications and variations will be apparent to those of ordinary skill in the art. Further, different illustrative embodiments may provide different features as compared to other desirable embodiments. The embodiment or embodiments selected are chosen and described in order to best explain the principles of the embodiments, the practical application, and to enable others of ordinary skill in the art to understand the disclosure for various embodiments with various modifications as are suited to the particular use contemplated.

What is claimed is:

1. A method for identifying a geometry for a shim, the method comprising:
    assembling a first part and a second part with a couplant positioned between the first part and the second part at a shim location, at which the shim is to be installed, by positioning the couplant over the first part at the shim location and positioning the second part over the couplant to form an assembly;
    positioning an ultrasonic device at each selected location of a set of selected locations at a selected side of the assembly;
    sending a pulse of ultrasonic energy into the assembly at each selected location of the set of selected locations along the assembly corresponding to the shim location using the ultrasonic device;
    detecting a plurality of echoes for the each selected location of the set of selected locations using data generated by the ultrasonic device in response to the ultrasonic device receiving reflections of the ultrasonic energy; and
    identifying the geometry for the shim based on the plurality of echoes detected at each selected location of the set of selected locations.

2. The method of claim 1 further comprising:
    applying a number of assembly loads to the assembly prior to sending the pulse of ultrasonic energy into the assembly.

3. The method of claim 1, wherein positioning the ultrasonic device comprises:
    positioning the ultrasonic device over a device coupling element that is positioned at the selected location at the selected side of the assembly.

4. The method of claim 1, wherein identifying the geometry of the shim comprises:
    identifying a time interval between a first time at which a first echo for the selected location of the set of selected locations is detected and a second time at which a second echo for the selected location is detected; and
    computing a distance between the first part and the second part at the selected location using the time interval.

5. The method of claim 1, wherein detecting the plurality of echoes comprises:
    receiving a reflection of at least a portion of the ultrasonic energy that is reflected at an interface between a device coupling element and the second part.

6. The method of claim 1, wherein detecting the plurality of echoes comprises:
    receiving a reflection of at least a portion of the ultrasonic energy that is reflected at an interface between the couplant and the first part.

7. The method of claim 6, wherein detecting the plurality of echoes comprises:
    receiving a reflection of at least a portion of the ultrasonic energy that is reflected at an interface between the couplant and the second part.

8. The method of claim 1, wherein assembling the first part and the second part comprises:
    placing a couplant over a shear tie at the shim location; and
    placing a panel for a wing of an aircraft over the couplant to form the assembly.

9. The method of claim 1 further comprising:
    generating the data using the ultrasonic device; and
    sending the data from the ultrasonic device to a data processor for processing.

10. The method of claim 9, wherein detecting the plurality of echoes comprises:
    detecting, by the data processor, the plurality of echoes.

11. The method of claim 1 further comprising:
    generating a shim model for the shim using the geometry identified for the shim.

12. The method of claim 1 further comprising:
    selecting the set of selected locations based on at least one of a size of the shim to be installed or a desired level of accuracy for the geometry of the shim.

13. A method for generating data for use in identifying a geometry of a shim, the method comprising:
    assembling a first part and a second part with a couplant positioned between the first part and the second part to form an assembly;
    positioning an ultrasonic device at each selected location of a set of selected locations at a selected side of the assembly;
    sending a pulse of ultrasonic energy into the assembly at each selected location of the set of selected locations along the assembly corresponding to a shim location using an ultrasonic device;
    receiving reflections of at least a portion of the ultrasonic energy that is reflected at interfaces formed within the assembly for the each of the set of selected locations back at the ultrasonic device; and
    generating data based on the reflections received at the ultrasonic device, wherein the data is sent to a data processor for processing to identify the geometry for the shim that is to be installed between the first part and the second part.

14. An apparatus comprising:
- an ultrasonic device positioned over an assembly that includes a first part, a second part, and a couplant positioned between the first part and the second part, wherein the ultrasonic device is configured to send a pulse of ultrasonic energy into the assembly at each of a set of selected locations along the assembly corresponding to a shim location, receive reflections of at least a portion of the ultrasonic energy that is reflected at interfaces within the assembly, and generate data for the reflections received; and
- a data processor that is configured to receive the data and identify a geometry for the shim using the data.

15. The apparatus of claim 14, wherein the couplant comprises at least one of a gel material, a rubber material, a film of glycerin, a film of rubber, or a fluid.

16. The apparatus of claim 14, wherein the first part has a rigid surface that comes into contact with the couplant and wherein the second part has a flexible surface that comes into contact with the couplant.

17. The apparatus of claim 14, wherein the first part is a shear tie and the second part is a panel for a wing of an aircraft.

18. The apparatus of claim 14, wherein the interfaces include at least one of an interface between the couplant and the first part, an interface between the couplant and the second part, or an interface between a device coupling element and the second part.

* * * * *